(12) United States Patent
Jung

(10) Patent No.: US 11,226,065 B1
(45) Date of Patent: Jan. 18, 2022

(54) ARTICULATED SUPPORT DEVICE

(71) Applicant: Kyu-Sung Jung, Seoul (KR)

(72) Inventor: Kyu-Sung Jung, Seoul (KR)

( * ) Notice: Subject to any disclaimer, the term of this patent is extended or adjusted under 35 U.S.C. 154(b) by 0 days.

(21) Appl. No.: 17/099,914

(22) Filed: Nov. 17, 2020

(30) Foreign Application Priority Data

Oct. 30, 2020 (KR) .................. 10-2020-0143199

(51) Int. Cl.
*F16M 11/12* (2006.01)
*F16M 11/18* (2006.01)
*A61B 1/00* (2006.01)
*F16C 1/10* (2006.01)

(52) U.S. Cl.
CPC ....... *F16M 11/121* (2013.01); *A61B 1/00149* (2013.01); *F16M 11/18* (2013.01); *F16C 1/10* (2013.01); *F16M 2200/066* (2013.01)

(58) Field of Classification Search
CPC ............. F16M 11/121; F16M 11/18; F16M 2200/066; F16M 2200/021; F16M 2200/022; F16C 1/10; A61B 1/00149; A61G 13/101; A61G 13/12; A61G 13/1205
USPC ..................................... 248/124.1
See application file for complete search history.

(56) References Cited

U.S. PATENT DOCUMENTS

| | | | |
|---|---|---|---|
| 7,337,808 B2 * | 3/2008 | Shamir | E03C 1/0408 138/120 |
| 7,730,565 B1 * | 6/2010 | Masson | A61G 13/101 5/646 |
| 9,782,316 B2 * | 10/2017 | Schuerch, Jr | F16C 11/10 |
| 10,072,793 B2 * | 9/2018 | Wyslucha | F16M 11/2007 |
| 10,918,551 B2 * | 2/2021 | Wyslucha | A61G 13/10 |
| 2008/0121765 A1 * | 5/2008 | Fetzer | A61B 90/50 248/122.1 |
| 2010/0030377 A1 * | 2/2010 | Unsworth | F16M 11/14 700/245 |

FOREIGN PATENT DOCUMENTS

JP H07-184916 A 7/1995

* cited by examiner

*Primary Examiner* — Christopher Garft
(74) *Attorney, Agent, or Firm* — KORUS Patent, LLC; Seong Il Jeong

(57) ABSTRACT

Disclosed herein is an articulated support device. The articulated support device is formed to include a plurality of links connected to each other. A device stand is detachably coupled to the front end of the articulated support device and the rear end of the articulated support device is fixedly coupled to a structure detachably. The connection portions of the plurality of links are fixed not to move relative to each other or the connection portions are released to be rotatable relative to each other through an operation of a handle part provided on a front side of the articulated support device. The articulated support device includes a plurality of rotation and fixing units. Each of the plurality of rotation and fixing units includes a front link connection adapter, a wire central binding portion, a rotation regulation portion, a casing pipe, and an inner connection pipe.

3 Claims, 9 Drawing Sheets

ARTICULATED SUPPORT DEVICE

CROSS-REFERENCE TO RELATED APPLICATION

This application claims the benefit of Korean Patent Application No. 10-2020-0143199 filed on Oct. 30, 2020, which is hereby incorporated by reference herein in its entirety.

BACKGROUND

1. Technical Field

The present invention relates generally to an articulated support device that is formed by connecting a plurality of links to each other, and more particularly to an articulated support device that may be securely fixed and supported in the exact position desired by the user, may conveniently and rapidly switch between fixing and releasing, may be easily manufactured and downsized and have excellent durability, may prevent the inflow of foreign substances into the inside thereof because the airtightness of the portions where the links are connected to each other is excellent, may allow precise movement and fixing, may be used repeatedly for a long time because the durability of units that perform rotation and fixing functions is particularly excellent, and may be conveniently assembled.

2. Description of the Related Art

In general, medical technology for small incisions has the advantage of minimizing a patient's recovery time, discomfort, and side effects by reducing the size of the external tissue damaged during surgery or diagnosis. Recently, as a more advanced micro-incision medical technology, Natural Orifice Transluminal Endoscopic Surgery (NOTES) has been proposed.

Normally, an endoscope device is a device that visually checks and diagnoses an abnormal area inside the human body. The endoscope device includes a hose having a certain length, a camera installed at the end of the hose, and a display unit configured to receive and display an image acquired from the camera.

As a representative medical technology using such an endoscopic device, there is a natural opening endoscopic surgery. Natural opening endoscopic surgery is a new surgical method in which an endoscopic device enters the human body through a natural opening such as the mouth, anus, or vagina, penetrates into the abdominal cavity through an organ such as the stomach or large intestine or accesses an organ such as the liver or gallbladder, and performs surgery. An articulated support device is used to support and fix such an endoscope device used in such surgery and to move freely. Through the articulated support device, it is possible to move flexibly and freely while the anterior endoscopic device enters the body. In contrast, while the endoscope is used for surgery after being completely inserted into the human body, the articulated support device securely fixes and supports the endoscopic device so as to block the movement of the endoscopic device.

Among conventional articulated support devices, there are some devices that fix an endoscopic device using frictional force so that it does not move during surgery. However, the fixing force of the devices is weak, so there are many difficulties during surgery. In order to overcome this problem, Korean Patent No. 10-1005830 (the title of the invention: "Elongated Articulated Device and Overlapping Link Constituting the Same") discloses an elongated articulated device in which a plurality of overlapping links are connected in series using an operating wire, an elastic lever, a latch slot, and a pressing force provision means and the overlapping links connected in series can be switched between a mutually released state and a mutually fixed state. However, this elongated articulated device has a problem in that a separate sealing means must be provided to prevent the entry of foreign substances because the connection portions between the overlapping links are opened and thus foreign substances can easily enter inside during the procedure. The elongated articulated device further has a problem in that vibration is generated during movement between steps because the articulated device is not fixed while moving linearly but is fixed in a number of steps and is formed to be fixed at predetermined fixed positions while moving step by step. The elongated articulated device further has a problem in that it is difficult to be accurately fixed at a desired position desired by a user because it is fixed at predetermined fixed points in multiple steps. The elongated articulated device further has a problem in that when the support weight is increased, the size of the articulated device must also be increased in order to increase the fixing force.

To overcome the above problem, Korean Patent No. 10-2143226 (the title of the invention: "Articulated Support Device"), which was filed and registered for a patent by the same inventor and applicant of the present invention, discloses an articulated support device that enables fixing at the exact position desired by a user and allows rapid switching between fixing and releasing. However, this articulated support device has a problem in that the outer circumferential surfaces of the rotating rollers or internal contact surfaces in contact with rotating rollers are broken and damaged due to the high fixing pressing force during fixing for a long time because the high pressing force for fixing is intensively applied to four rotating rollers provided inside a unit that performs rotation and fixing. The articulated support device further has a problem in that there is a difficulty in assembling the wire in a sufficiently pulled state without any loosening margin during production assembly for the purpose of rapid and precise fixing and release operation because the movement range of the operating wire is narrow. The articulated support device further has a problem in that even during operation, excessive pulling force is applied to a wire even by the operation of slightly pressing a handle part and thus the wire is cut in a short operating time because the movement range of the wire is excessively narrow.

SUMMARY

The present invention has been conceived to overcome the above-described problems, and an object of the present invention is to provide an articulated support device that enables precise movement and fixing by being linearly moved and immediately fixed to a desired position, may prevent foreign substances from entering the device during a procedure by sealing the parts where the plurality of links constituting the support device are connected to each other.

In particular, an object of the present invention is to provide an articulated support device that may improve the durability of rotating and fixing units by distributing the high pressing force applied onto rotating rollers provided inside the units for performing rotation and fixing among rotating rollers and may make the movement range of the operating wire longer, thereby preventing excessive pulling force from being concentrated and generated in the initial stage of an operation even in spite of the pressing operation of a handle part for releasing fixing and also preventing the phenomenon that an operating wire is cut in a short time.

According to an aspect of the present invention, there is provided an articulated support device, the articulated support device being formed to include a plurality of links connected to each other, in which a device stand is detachably coupled to a front end of the articulated support device and a rear end of the articulated support device is fixedly coupled to a structure detachably, and connection portions of the plurality of links are fixed not to move relative to each other or the connection portions of the plurality of links are released to be rotatable relative to each other through an operation of a handle part provided on a front side of the articulated support device, the articulated support device including a plurality of rotation and fixing units, wherein each of the plurality of rotation and fixing units includes: a front link connection adapter formed to have an inner hollow, and configured such that a front thereof is detachably coupled to an opposite side of the front link; a wire central binding portion formed to have an inner hollow, and is configured such that the operating wire is provided to pass through this inner hollow, a forward/rearward movable body provided with a coil spring seating portion therein is provided in the front of the wire central binding portion and is formed to move forward and rearward together with the operating wire, a front cover is provided at a position spaced apart by a predetermined distance in front of the forward/rearward movable body so that it is rotatable in front of the inner hollow of the front link connection adapter but does not move forward or rearward, a forward/rearward elastic spring formed of an inner hollow coil spring is seated on the coil spring seat so that the operating wire passes through this inner hollow, and a front surface of the forward/rearward elastic spring is provided to be in contact with a front of the inner side of the front cover and a rear surface of the forward/rearward elastic spring is provided to be in contact with a rear of the inner side of the coil spring seat; a rotation regulation portion provided on a circumferential surface of the wire central binding portion to be rotated together with the wire central binding portion, and also provided in an inner hollow of the front link connection adapter so that rotational movement is regulated according to forward and rearward the movement of the wire central binding portion; a casing pipe provided such that a front of the forward connection adapter passes through an inner hollow of the casing pipe and protrudes by a predetermined length, also rotatably provided around the forward connection adapter, and configured such that a rear side of the casing pipe is detachably coupled to one side of the rear link; and an inner connection pipe provided such that a front of the wire central binding portion passes through an inner hollow of the inner connection pipe and a rear of the wire central binding portion is located in this inner hollow and provided to rotate together, and formed in a rear of the inner hollow of the casing tube to rotate together with the casing tube; wherein the plurality of links are formed to have an inner hollow; wherein the front link and the rear link are connected to each other through the rotation and fixing units, the handle part is provided on one side of a front of the foremost one of the plurality of links and the fixing portion configured to be detachably coupled to a structure is provided on an opposite side of a rearmost link, a rear end of the operating wire is fixedly coupled to one side of a rear of an inner hollow of the rearmost one of the plurality of links, and a front of the operating wire passes through the inner hollows of the plurality of links, is wound around the wire fixing ring of each rotation and fixing unit, then passes through the wire central binding portion, and is connected to the handle part; wherein a pressure operation portion is provided on one side of the handle part so that, when the pressure operation portion is pressed, the front of the operating wire is pulled, and thus a wire and wire central binding portion of each of the rotation and fixing units connecting the plurality of links to each other are moved forward and so that, when the wire central binding portion is moved forward by forward pulling of the operating wire, the rotation regulation portion is released such that it is rotatable in the inner hollow of the forward connection adapter, with the result that, as the rotation regulation portion is released to be rotatable, the wire central binding portion, the inner connecting pipe, and the casing pipe are released to be rotatable together, so that the plurality of links are rotatable relative to each other; and, wherein when pressing force pressing the pressure operation portion of the handle part is removed, the operating wire, which has been pulled forward, is moved rearward together with the wire central binding portion by restoration elastic force of the forward/rearward elastic spring of each of the rotation and fixing units, and, when the wire central binding portion is moved rearward, the rotation regulation portion is fixed not to be rotated in the inner hollow of the forward connection adapter, so that, as the rotation regulation portion is fixed, the wire central binding portion, the inner connecting pipe, and the casing pipe are fixed together, with the result that the plurality of links are fixed not to be rotated relative to each other.

In the articulated support device according to the aspect of the present invention, a rotating roller seating protrusion having an inner hollow is provided to protrude by a predetermined distance in front of the inner connection pipe, a fixing ring coupling protrusion is formed on a front surface of the rotating roller seating protrusion to protrude by a predetermined distance, rotating roller plane movement surfaces are formed on upper, lower, left, and right outer surfaces of the rotating roller seating protrusion, respectively, rotating roller stop protruding surfaces are formed to protrude as predetermined curved surfaces on outer surfaces between the rotating roller plane movement surfaces, and a pressing protrusion rod fixing groove is formed on one side of each of the rotation roller stop protrusion surfaces; the rotation regulation portion includes: a pressure protrusion rod formed as a circular rod having a predetermined length, and configured such that one end thereof is fixedly coupled into the pressure protrusion rod fixing groove; a guide piece coupling ring fixedly coupled to an outer circumferential surface of the wire central binding portion; an opposite side guide piece ring formed in a ring shape, rotatably coupled to a rear outer circumferential surface of the guide piece coupling ring, and configured such that four opposite side guide pieces are provided to protrude by a predetermined length rearward at predetermined intervals on a rear of the opposite side guide piece ring and an opposite side protruding rod guide groove is formed in front of the opposite side guide piece; a one side guide piece ring formed in a ring shape, rotatably coupled to a front outer circumferential surface of the guide piece coupling ring, and configured such that four one side guide pieces are provided to protrude by a predetermined length rearward at predetermined intervals on a rear of the one guide piece ring and are formed to come into contact with an one side surface on which the opposite side protruding rod guide groove of the opposite side guide piece is formed and an one side protruding rod guide groove is formed in front of a surface in contact with the one side surface on which the opposite side protruding rod guide groove of the opposite side guide piece is formed and is also provided to be opposite to the opposite side protruding rod guide groove; a fixing ring formed in an inner hollow ring shape, fixedly coupled to the fixing ring coupling protrusion of the inner connection pipe, is configured such that four rotating roller separation prevention pieces are provided on the outer circumferential surface of the fixing ring at predetermined intervals, guide piece movement grooves are formed between the four rotating roller separation prevention pieces, and a pair of the one side guide piece and the opposite side guide piece vertically pass through the guide piece movement groove and are movable while being spaced apart from each other in the state of being contact with each other until the sides of the respective guide pieces come into contact with left and right groove inner sides of the movement groove; a rotating roller elastic pressure rib coupled in such a manner that a front thereof comes into contact with and is fixedly coupled to a center of the rear surface of the rotation roller separation prevention piece of the fixing ring, provided along a longitudinal direction of the rotating roller seating protrusion in a center of the horizontal movement surface of the rotating roller, and configured such that a pair of elastic pressing pieces are formed on both left and right sides of the rotating roller elastic pressing rib; and rotating rollers provided on left and right sides of the rotating roller elastic pressing rib along a longitudinal direction, and also provided such that inner sides of the rotating rollers come into contact with the elastic pressing piece and outer sides thereof come into contact with one of the one side guide piece and the opposite side guide piece; and the opposite side protruding rod guide groove and the one side protruding rod guide groove face each other and form a protruding rod guide groove in a state in which the one side and opposite side guide pieces are in contact with each other, and the pressing protruding rod is provided to vertically pass through the protruding rod guide groove and protrude to an outside.

Preferably, the handle part includes: a handle body portion provided with an inner reception space, and configured such that a pressing operation portion insertion hole is formed therethrough to a predetermined length along a longitudinal direction on one side thereof; a pressure operation portion configured such that a front thereof is inserted and rotatably hinged into the handle body through the pressure operation portion insertion hole and a rear thereof is provided to pass through the pressure operation portion insertion hole and protrude to an outside; an upper pressure roller rotatably provided on one side of a front of the pressure operation portion inserted into the handle body portion; and a lower pressure roller rotatably provided in the handle body portion at a position spaced apart from the upper pressure roller downward by a predetermined distance; when a front of the operating wire passes between the upper pressing roller and the lower pressing roller while being in contact with outer surfaces of the rollers and is then fixedly coupled to an inner front of the handle part and a rear of the pressure operation portion protruding to an outside is pressed with a predetermined pressing force and rotated downward around the front hinge coupling portion, the upper pressure roller moves downward together with the pressure operation portion, presses the operating wire, passing while being in contact with a lower side of the upper pressure roller, toward the lower pressure roller and pulls the operating wire forward; and when predetermined pressing force pressing a rear of the pressure operation portion downward is released, the pressure operation portion is moved backward while being relaxed by elastic restoration force of the wire, and rears of the upper pressure roller and the pressure operation portion are returned to an upper side.

BRIEF DESCRIPTION OF THE DRAWINGS

The above and other objects, features, and advantages of the present invention will be more clearly understood from the following detailed description taken in conjunction with the accompanying drawings, in which.

DETAILED DESCRIPTION

Figure 1:
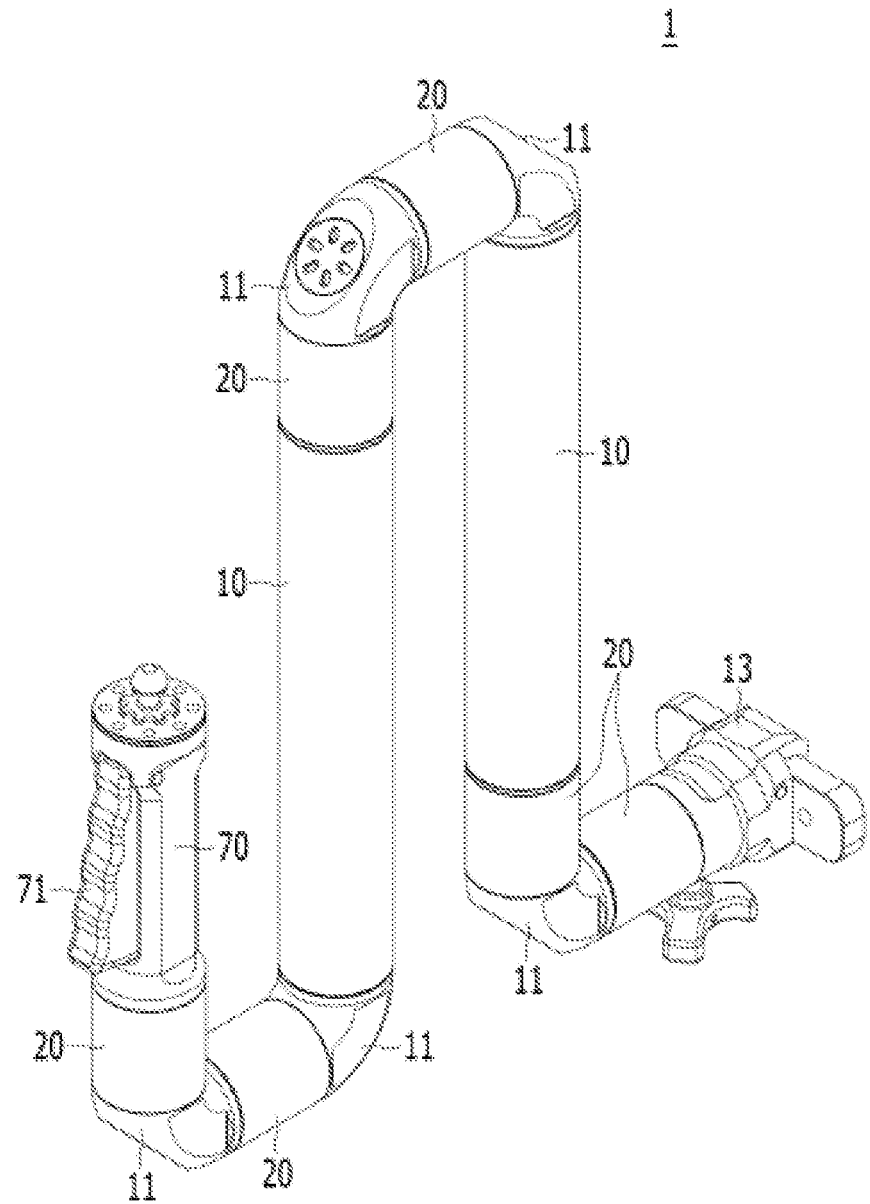
FIG. 1 is a perspective view showing an articulated support device according to the present invention.

Embodiments of the present invention in which the above objects can be realized in detail will be described below with reference to the accompanying drawings. In the following description of the embodiments, the same names and reference numerals are used for the same components, and additional descriptions thereof will be omitted below.

Figure 2:
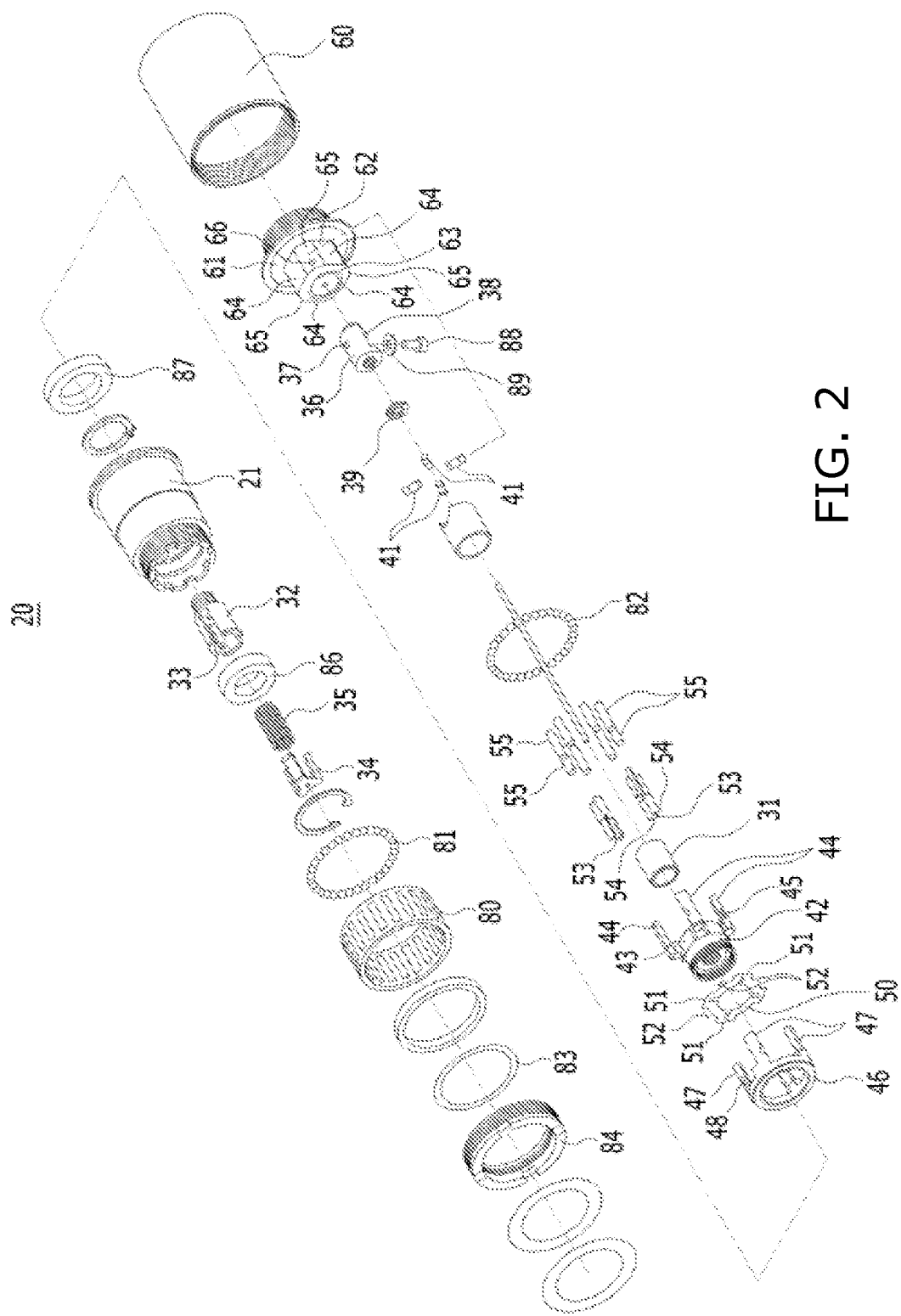
FIG. 2 is an exploded perspective view showing a rotation and fixing unit in the articulated support device according to the present invention.
Figure 2A:
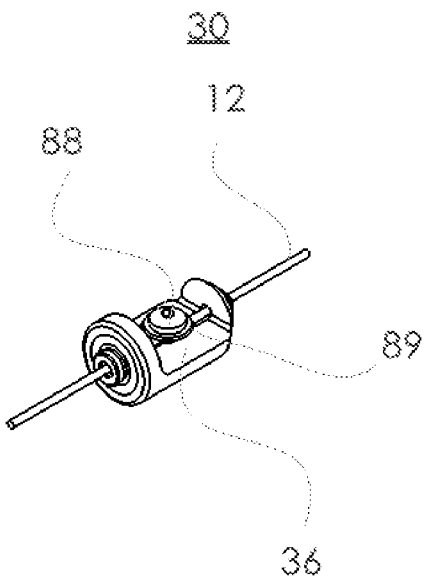
FIG. 2A is a perspective view showing a wire central binding portion of the rotation and fixing unit according to the present invention.
Figure 2B:
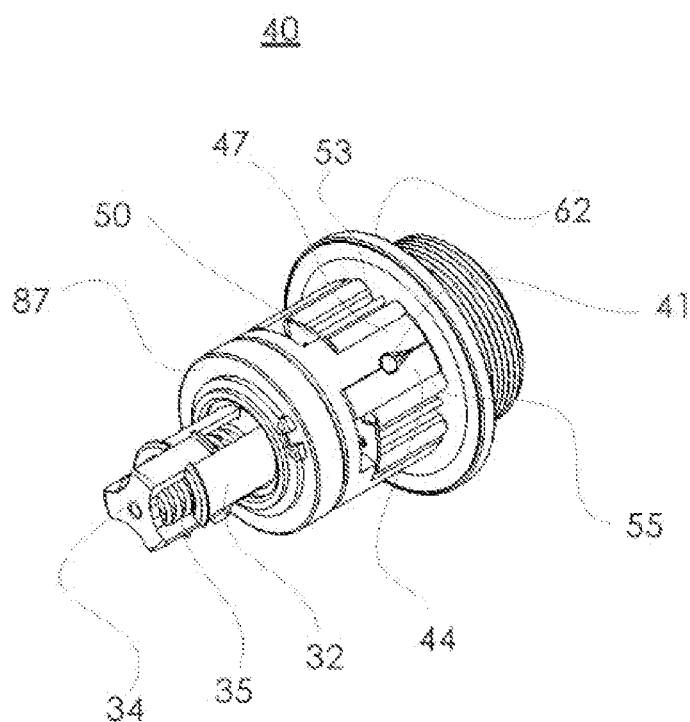
FIG. 2B is a perspective view showing a rotation regulation portion of the rotation and fixing unit according to the present invention.
Figure 3:
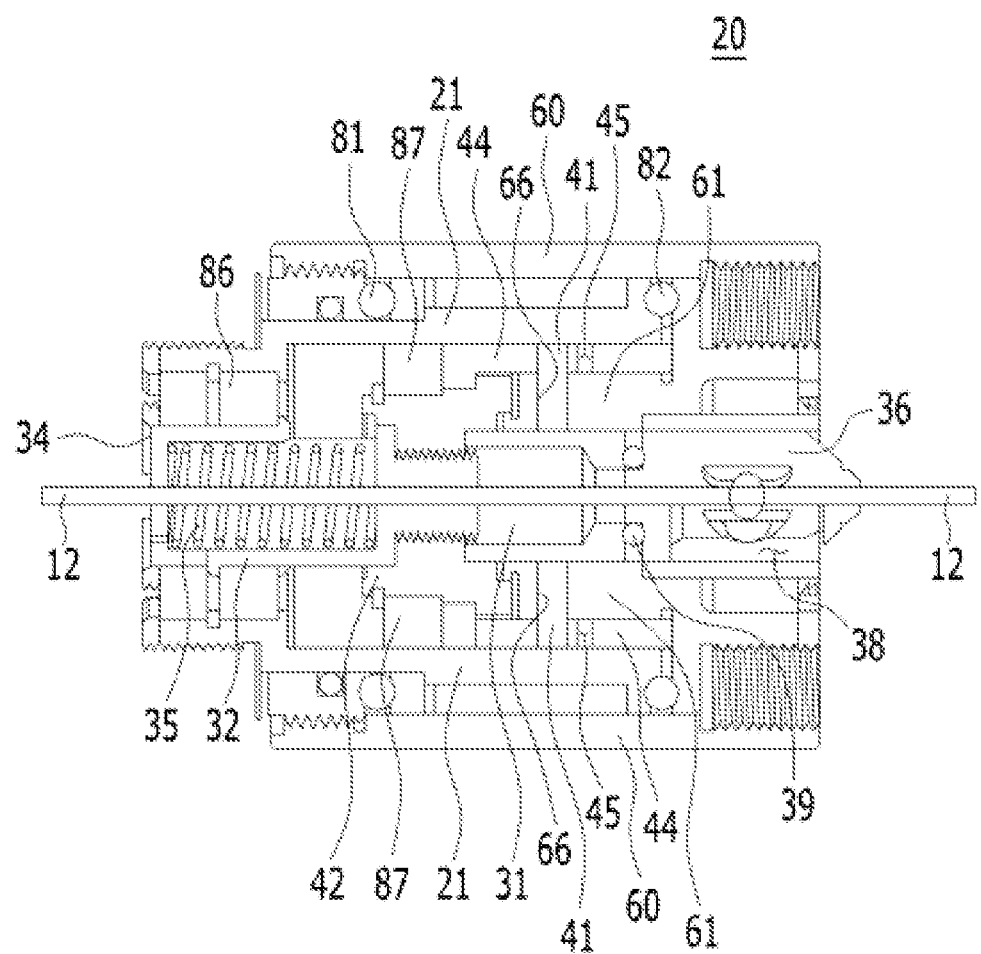
FIG. 3 is a sectional view showing the rotation and fixing unit in the articulated support device according to the present invention.

FIG. 1 is a perspective view showing an articulated support device 1 according to the present invention; FIG. 2 is an exploded perspective view showing a rotation and fixing unit 20 in the articulated support device 1 according to the present invention; FIG. 2A is a perspective view showing a wire central binding portion 30 of the rotation and fixing unit 20 according to the present invention; FIG. 2B is a perspective view showing a rotation regulation portion 40 of the rotation and fixing unit 20 according to the present invention; and FIG. 3 is a sectional view showing the rotation and fixing unit 20 in the articulated support device 1 according to the present invention.

Figure 4:
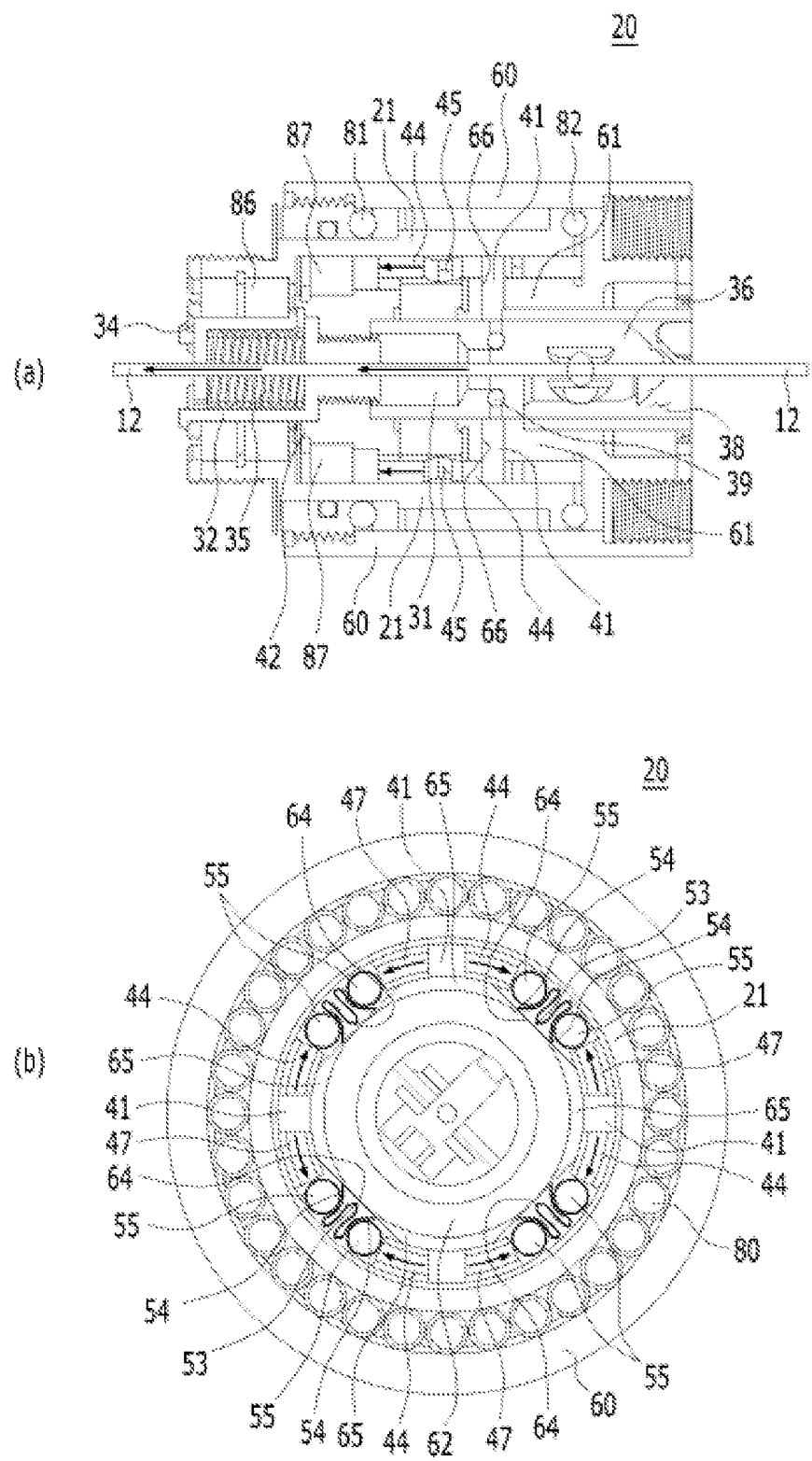
FIG. 4 shows longitudinal-sectional and cross-sectional views depicting the internal operation of a rotation and fixing unit in which in the articulated support device according to the present invention, when the pressure operation portion of a handle part is pressed, an operating wire is pulled forward, released, and becomes rotatable.
Figure 5:
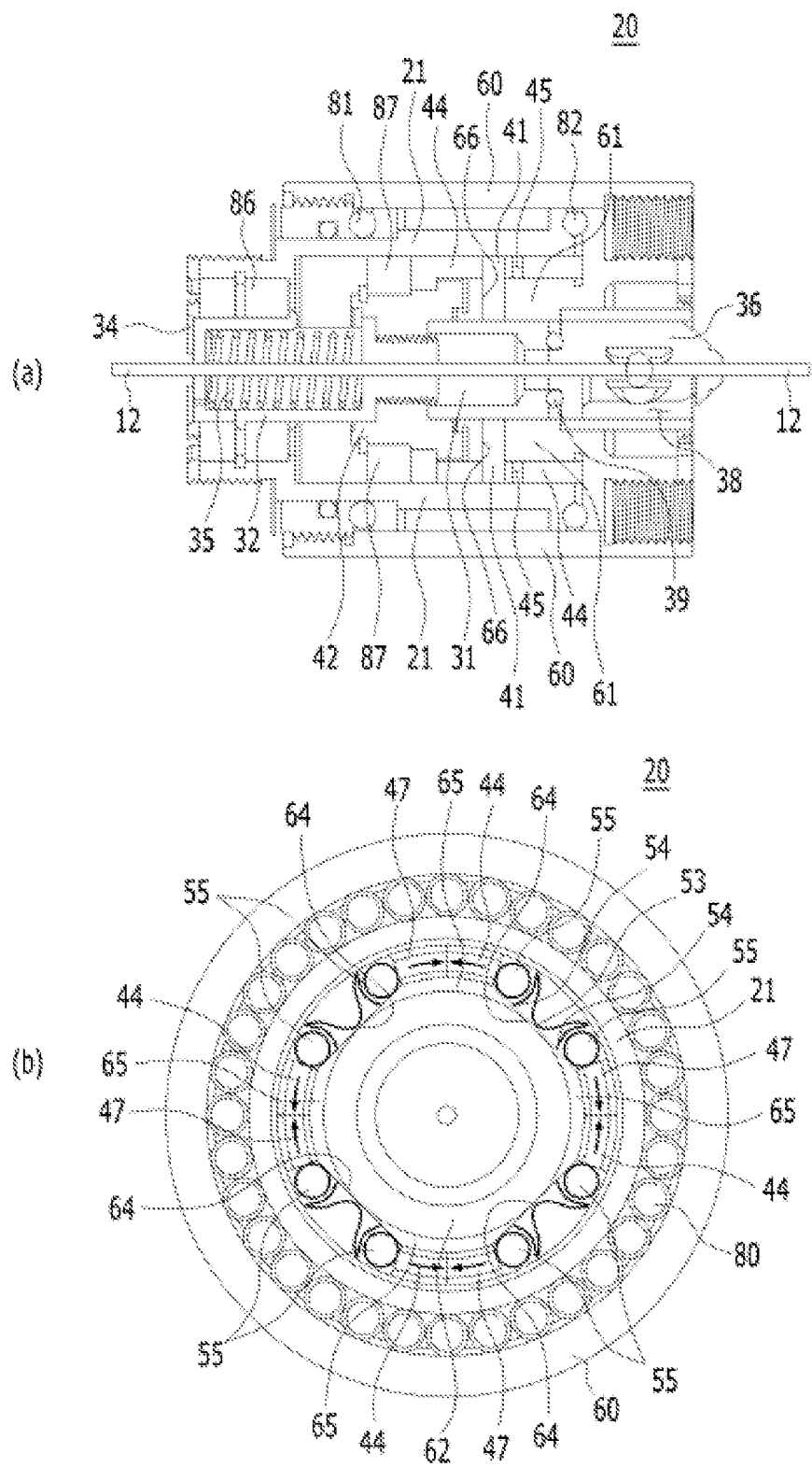
FIG. 5 shows longitudinal-sectional and cross-sectional views depicting the internal operation of the rotation and fixing unit in which in the articulated support device according to the present invention, when the pressing force pressing the pressure operation portion of the handle part is released, the operating wire pulled forward is moved back and fixed in position.
Figure 6:
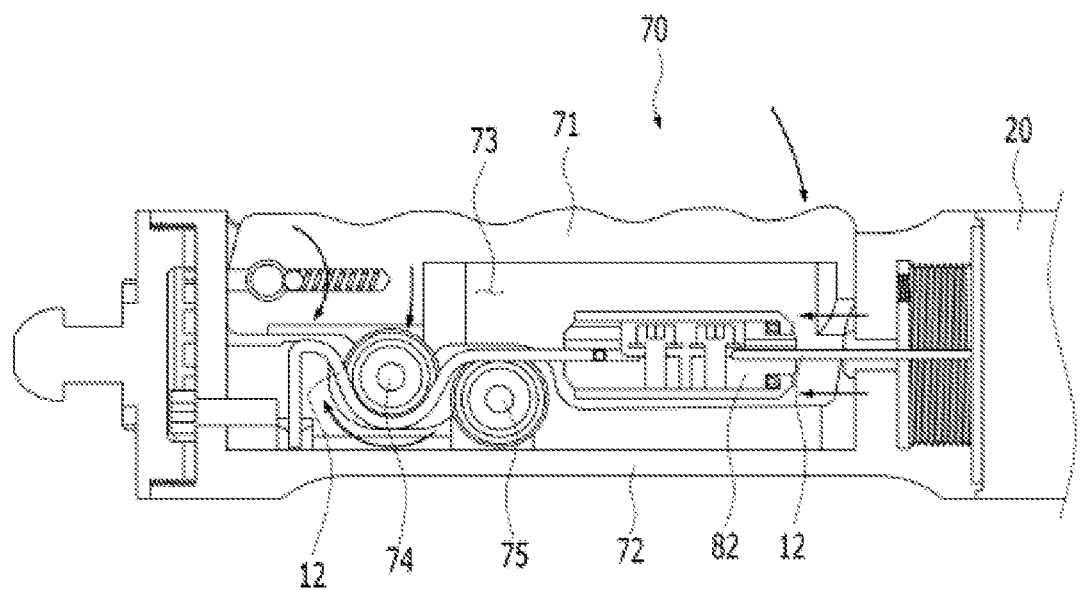
FIG. 6 is a view showing an internal operation in which in the articulated support device according to the present invention, when the pressure operation portion of the handle part is pressed, the operating wire is pulled forward.

FIG. 4 shows a longitudinal-sectional view and cross-sectional view depicting the internal operation of a rotation and fixing unit 20 in which in the articulated support device 1 according to the present invention, when the pressure operation portion of a handle part is pressed, an operating wire 12 is pulled forward, released, and becomes rotatable; FIG. 5 shows a longitudinal-sectional view and cross-sectional view depicting the internal operation of the rotation and fixing unit 20 in which in the articulated support device 1 according to the present invention, when the pressing force pressing the pressure operation portion of the handle part is released, the operating wire 12 pulled forward is moved back and fixed in position; and FIG. 6 is a view showing an internal operation in which in the articulated support device 1 according to the present invention, when the pressure operation portion of the handle part is pressed, the operating wire 12 is pulled forward.

Figure 7:
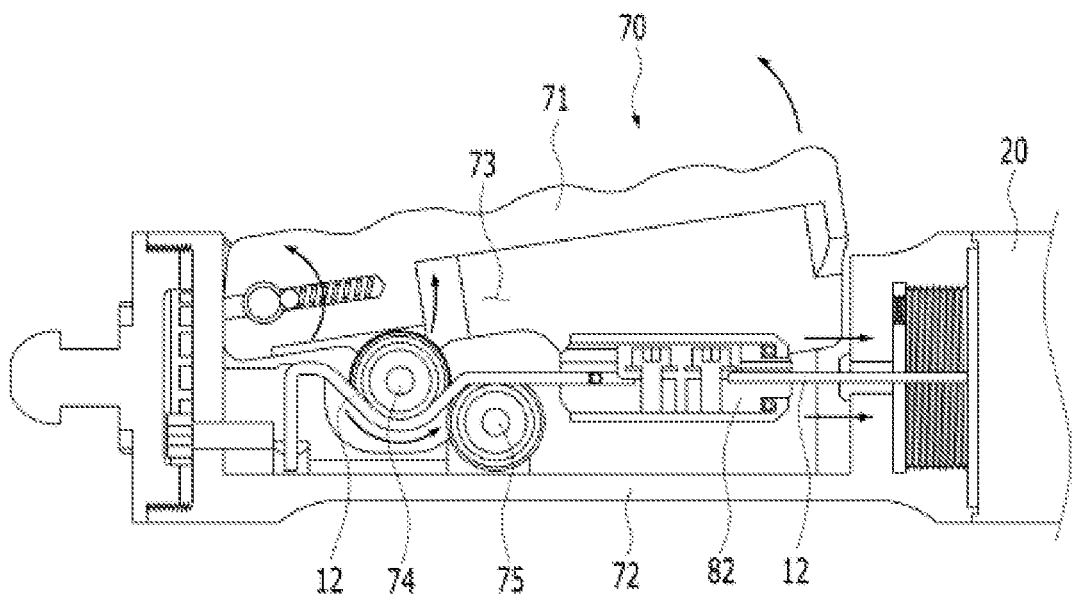
FIG. 7 is a view showing an internal operation in which in the articulated support device according to the present invention, when the pressing force pressing the pressure operation portion of the handle part is released, the operating wire pulled forward is moved back.
Figure 8:
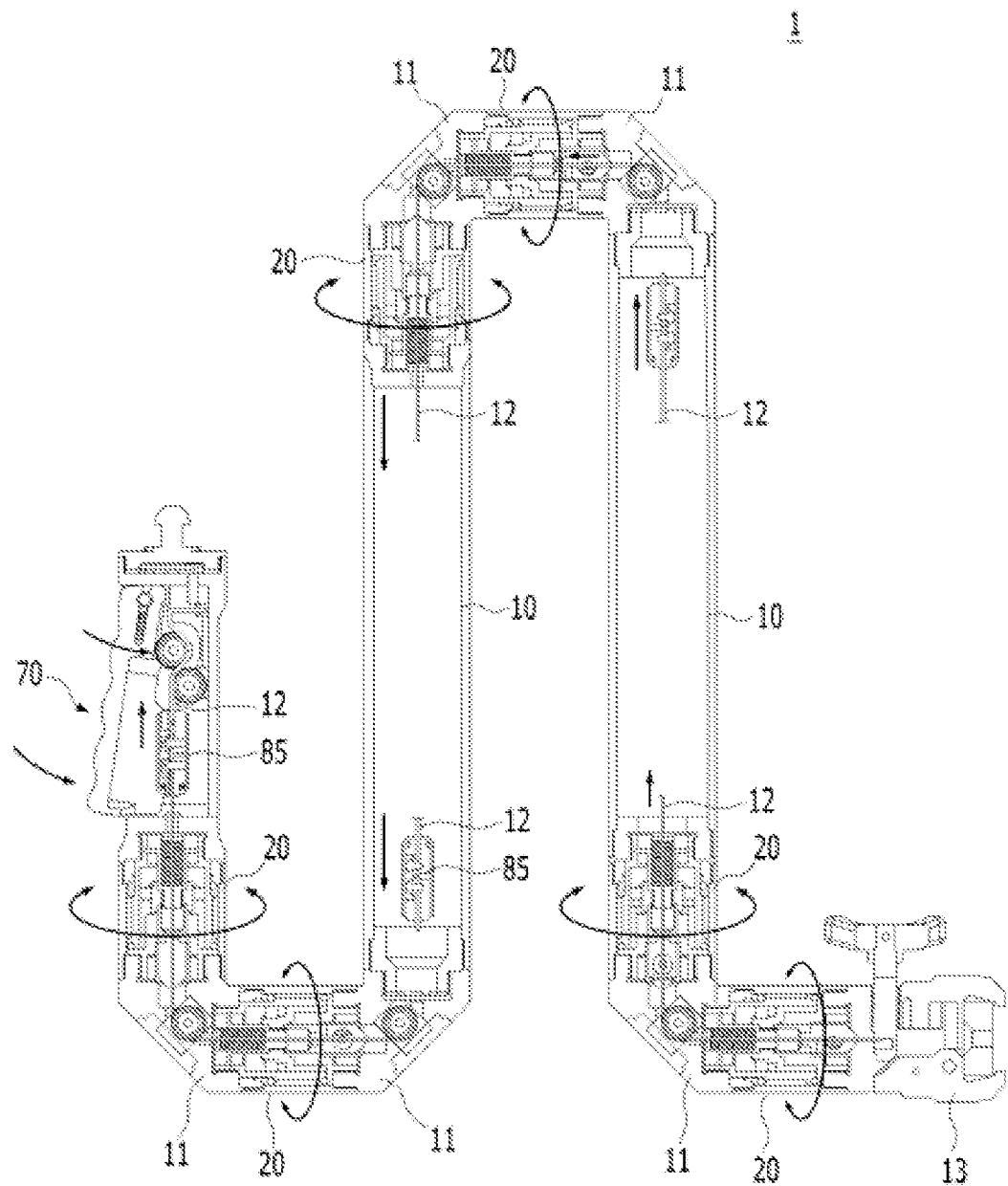
FIG. 8 is a view showing an internal operation in which when the fixing of the articulated support device 1 according to the present invention is released, rotational movement is performed through rotation and fixing units connecting a plurality of links 10 to each other.
Figure 9:
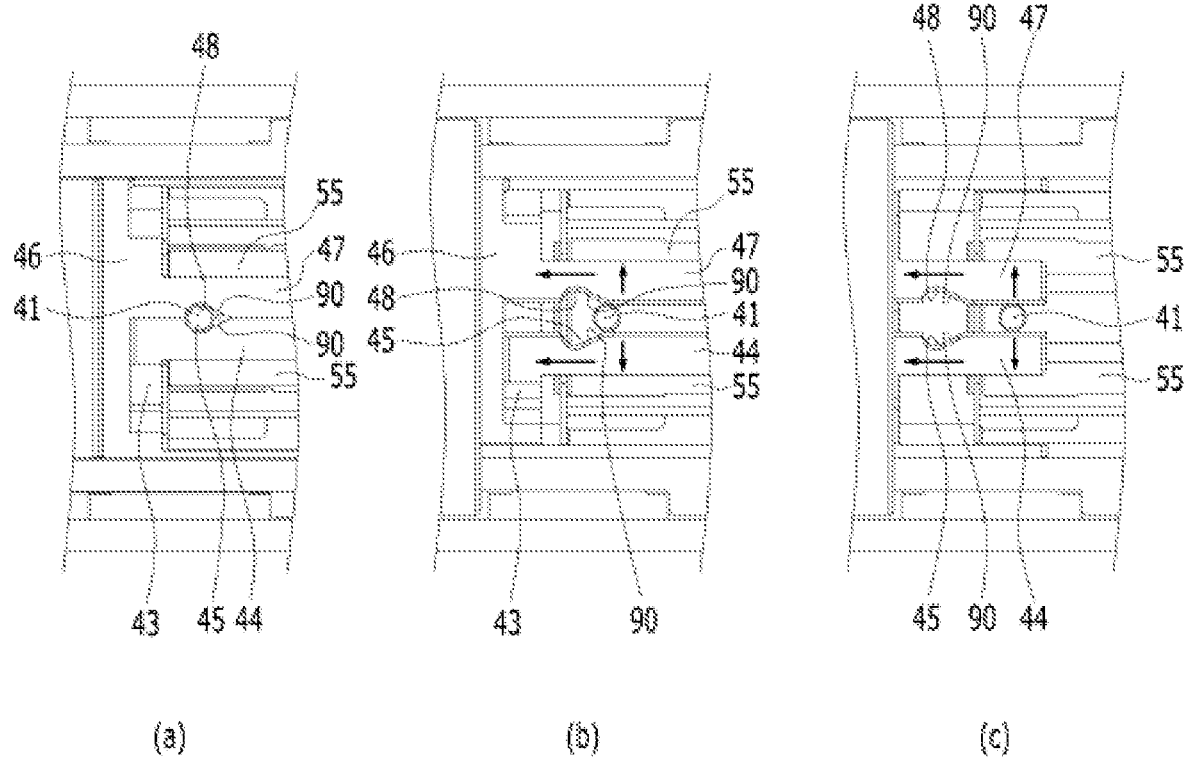
FIG. 9 is a view showing an internal operation in which in the rotation regulation portion of the articulated support device according to the present invention, when fixing is released, a pressure protruding rod comes out of a protruding rod guide groove, and is interposed between one side and opposite side guide pieces, and moves the respective guide pieces to left and right sides.

FIG. 7 is a view showing an internal operation in which in the articulated support device 1 according to the present invention, when the pressing force pressing the pressure operation portion of the handle part is released, the operating wire 12 pulled forward is moved back; FIG. 8 is a view showing an internal operation in which when the fixing of the articulated support device 1 according to the present invention is released, rotational movement is performed through rotation and fixing units 20 connecting a plurality of links 10 to each other; and FIG. 9 is a view showing an internal operation in which in the rotation regulation portion of the articulated support device 1 according to the present invention, when fixing is released, a pressure protruding rod 41 comes out of a protruding rod guide groove 49, and is interposed between one side and opposite side guide pieces 47 and 44, and moves the respective guide pieces to left and right sides.

The articulated support device 1 according to the present invention is formed to include a plurality of links 10 connected to each other, a device stand is detachably coupled to the front end of the articulated support device 1 and the rear end of the articulated support device 1 is fixedly coupled to a structure detachably, and the connection portions of the plurality of links 10 are fixed not to move relative to each other or the connection portions of the plurality of links 10 are released to be rotatable relative to each other through the operation of a handle part 70 provided on the front side of the articulated support device 1.

As shown in FIGS. 1, 2 and 8, the articulated support device basically includes: the plurality of links 10 formed to have an inner hollow; the handle part 70 provided on the front one 10 of the plurality of links 10; a fixing part 13 provided at the rear end of the rear one 10 of the plurality of links and configured to fix the articulated support device 1 to the structure detachably; and the plurality of rotation and fixing units 20 configured to connect the plurality of links to each other.

The plurality of rotation and fixing units 20 connect the plurality of links 10, forming the articulated support device 1 according to the present invention, to each other, and are important components that selectively release the front and rear connection links connected via the rotation and fixing unit 20 so that they are rotatable relative to each other and fix the front and rear connection links so that they are not moved relative to each other.

As shown in FIGS. 2 and 3, each of the rotation and fixing units 20 is provided with a front link connection adapter 21 which is formed to have an inner hollow and the front of which is detachably screwed into the opposite side of the front link 10. A wire central binding portion 30 formed to have an inner hollow and provided such that an operating wire 12 passes through the inner hollow is configured to move forward and rearward together with the operating wire 12.

As shown in FIGS. 2 and 3, the wire central binding portion 30 is formed to have an inner hollow, the operating wire 12 is provided to pass through this inner hollow, and a forward/rearward movable body 32 provided with a coil spring seating portion 33 therein is provided in the front of the wire central binding portion 30 and is formed to move forward and rearward together with the operating wire 12. A front cover 34 is provided at a position spaced apart by a predetermined distance in front of the forward/rearward movable body 32 so that it is rotatable in front of the inner hollow of the front link connection adapter 21 but does not move forward or rearward. A forward/rearward elastic spring formed of an inner hollow coil spring is seated on the coil spring seat 33 so that the operating wire 12 passes through this inner hollow. The front surface of the forward/rearward elastic spring 35 is provided to be in contact with the front of the inner side of the front cover 34 and the rear surface of the forward/rearward elastic spring 35 is provided to be in contact with the rear of the inner side of the coil spring seat 33. A binding portion fastening pipe 31 having an inner hollow is fixedly coupled to the rear of the forward/rearward movable main body 32, and the operating wire 12 passes through this inner hollow and is provided to be movable forward and rearward together with the forward/rearward movable body 32.

That is, when the operating wire 12 passing through the wire central binding portion 30 moves forward, the binding portion fastening pipe 31 and the forward/rearward movable body 32 compress the forward/rearward elastic spring 35 seated on the coil spring seating portion 33 toward the front surface of the front cover 34 while moving forward together with the operating wire 12. In this state, the front cover 34, the forward/rearward movable main body 32, and the binding portion fastening pipe 31 are rotatably provided within the inner hollow of the front link connection adapter 21.

Preferably, as shown in FIGS. 2 and 3, a wire fixing ring 36 having an inner hollow is provided at a position spaced apart by a predetermined distance from the rear surface of the binding portion fastening pipe 31, a coupling hole 37 into which a wire fixing screw 88 is screwed is formed on one side of the inner hollow of the wire fixing ring 36 to communicate with the inner hollow formed so that a part there is exposed to the outside, a wire seating groove 38 having a predetermined depth is formed around a portion, where the coupling hole 37 is partially exposed to the outside, so that the operating wire 12 wound around the outer circumferential surface of the wire fixing screw 88 a predetermined number of times is seated. The operating wire 12 passes through the wire fixing ring 36 and the binding portion fastening pipe 31 in the state of being wound around the wire fixing screw 88 a predetermined number of times, so that the degree of tension of the operating wire 12 can be adjusted by the number of times the wire is wound around the wire fixing screw 88. A wire fixing ring rotating bearing 39 is provided between the rear side of the binding portion fastening pipe 31 and the front surface of the wire fixing ring 36, so that the operating wire 12 is prevented from being twisted while articulated support device 1 rotates. As the operating wire 12 moves forward or rearward, the wire fixing ring 36 and the binding portion fastening pipe 31 are also moved forward or rearward together.

Furthermore, in a state in which the wire wound around the wire fixing screw 88 a predetermined number of times is seated in the wire seating groove 38, the wire be fixed by screwing the wire fixing screw 88 into the coupling hole 37. In this case, a copper washer 89 made of a material having a lower hardness than the operating wire 12 is interposed between the contact surface of the head of the wire fixing screw 88 and the wire, thereby minimizing damage to the wire surface by preventing the operating wire 12 from being pressed directly by the head of the fixing screw 88 due to excessive screw fastening force of the wire fixing screw 88.

A rotation regulation portion 40 is provided on the circumferential surface of the wire central binding portion 30 to be rotated together with the wire central binding portion 30, and is provided in the inner hollow of the front link connection adapter 21 so that the rotational movement is regulated according to the forward and rearward the movement of the wire central binding portion 30.

The casing pipe 60 is formed to have an inner hollow, is provided such that the front of the forward connection adapter 21 passes through this inner hollow and protrudes by a predetermined length, and is rotatably provided around the forward connection adapter 21, the rear side of the casing pipe 60 is detachably screwed to the front side of the rear link 10, so that when the casing pipe 60 rotates, the link 10 connected to the rear side of the casing pipe 60 also rotates, and the link 10 connected to the rear side of the casing pipe 60 is also fixed when the casing pipe 60 is fixed.

The inner connection pipe 61 is formed to have an inner hollow, is provided such that the front of the wire central binding portion 30 passes through the inner hollow and the rear of the wire central binding portion 30 is located in this inner hollow and provided to rotate together with the inner connection pipe 61, is formed in the rear of the inner hollow of the casing tube 60 to rotate together with the casing tube 60, and is provided to be rotated or fixed when the wire central binding portion 30, the inner connection pipe 61 and the casing pipe 60 move.

Preferably, as shown in FIGS. 3, 4 and 5, a rotating roller seating protrusion 62 having an inner hollow is provided to protrude a predetermined distance in front of the inner connection pipe 61, a fixing ring coupling protrusion 63 is formed on the front surface of the rotating roller seating protrusion 62 to protrude by a predetermined distance, rotating roller plane movement surfaces 64 are formed on the upper, lower, left, and right outer surfaces of the rotating roller seating protrusion 62, respectively, rotating roller stop protruding surfaces 65 are formed to protrude as predetermined curved surfaces on outer surfaces between the rotating roller plane movement surfaces 64, and a pressing protrusion rod fixing groove 66 is formed on one side of each of the rotation roller stop protrusion surfaces 65.

In the rotation regulation portion 40, one end of the pressure protrusion rod 41 formed as a circular rod having a predetermined length is fixedly coupled into the pressure protrusion rod fixing groove 66, the guide piece coupling ring 42 is fixedly coupled to the outer circumferential surface of the wire central binding portion 30, the opposite side guide piece ring 43 formed in a ring shape is rotatably coupled to the rear outer circumferential surface of the guide piece coupling ring 42, four opposite side guide pieces 44 are provided to protrude by a predetermined length rearward at predetermined intervals on the rear of the opposite side guide piece ring 43, and an opposite side protruding rod guide groove 45 is formed in front of the opposite side guide piece 44. A one side guide piece ring 46 formed in a ring shape is rotatably coupled to the front outer circumferential surface of the guide piece coupling ring 42, four one side guide pieces 47 are provided to protrude by a predetermined length rearward at predetermined intervals on the rear of the one guide piece ring 46 and are formed to come into contact with an one side surface on which the opposite side protruding rod guide groove 45 of the opposite side guide piece 44 is formed, and an one side protruding rod guide groove 48 is formed in front of a surface in contact with the one side surface on which the opposite side protruding rod guide groove 45 of the opposite side guide piece 44 is formed and is provided to be opposite to the opposite side protruding rod guide groove 45.

Furthermore, the fixing ring coupling protrusion 63 of the inner connection pipe 61 is fitted and fixedly coupled into the inner hollow of the fixing ring 50 formed in an inner hollow ring shape, four rotating roller separation prevention pieces 51 are formed to protrude at predetermined intervals on the outer circumferential surface of the fixing ring coupling protrusion 63, guide piece movement grooves 52 are formed between the four rotating roller separation prevention pieces 51, a pair of the one side guide piece 47 and the opposite side guide piece 44 pass through the guide piece movement groove 52 and are movable while being spaced apart from each other in the state of being in contact with each other until the sides of the respective guide pieces come into contact with the inner sides of the left and right grooves of the movement groove 52. The front of the rotating roller elastic pressure rib 53 comes into contact with and is fixedly coupled to the center of the rear surface of the rotation roller separation prevention piece 51 of the fixing ring 50, the rotating roller elastic pressure rib 53 is provided along the longitudinal direction of the rotating roller seating protrusion 62 in the center of the horizontal movement surface of the rotating roller, and a pair of elastic pressing pieces 54 are formed on both left and right sides of the rotating roller elastic pressing rib 53. Rotating rollers 55 are provided on the left and right sides of the rotating roller elastic pressing rib 53 along the longitudinal direction, and are provided such that the inner sides of the rotating rollers 55 come into contact with the elastic pressing piece 54 and the outer sides thereof come into contact with one of the one side guide piece 47 and the opposite side guide piece 44. The opposite side protruding rod guide groove 45 and the one side protruding rod guide groove 48 face each other and form a protruding rod guide groove in a state in which the one side and opposite side guide pieces 44 and 47 are in contact with each other, and the pressing protruding rod 41 is provided to vertically pass through the protruding rod guide groove 49 and protrude to the outside by a predetermined length.

As shown in the drawings, when the operating wire 12 is pulled forward, the binding portion fastening pipe 31, the forward/rearward movement body 32, the guide piece coupling ring 42, the one side and opposite side guide piece rings 43 and 46 and the one side and opposite side guide pieces 44 and 47 move forward together and compress the forward/rearward elastic spring 35 against the front cover 34.

When the operating wire 12 is pulled forward and thus the one side and opposite side guide pieces 44 and 47 move forward together, the protruding rod guide groove 49 is also moved forward together with the guide pieces. In this case, the pressure protruding rod 41 that passes through the protruding rod guide groove 49 and protrudes to the outside leaves the guide groove from a fixed and stopped state and is relatively moved to a position behind the one side and opposite side guide pieces 44 and 47 due to the forward movement of the protruding rod guide groove 49. In the process of changing the relative position, the pressure protruding rod 41 divides the one side and opposite side guide pieces 44 and 47 in contact with each other, and moves the one side and opposite side guide pieces 44 and 47 apart from each other to the left and right groove inner surfaces of the guide piece moving groove 52, respectively, by the radius of the pressure protruding rod 41 interposed between the one side and opposite side guide pieces 44 and 47. The rotating rollers 55 in contact with the outer sides of the guide pieces are pressed and moved to the center of the rotating roller plane moving surface 64 by a force higher than the elastic force of the elastic pressing piece 54. In the center of the rotating roller plane moving surface 64 to which the rotating rollers 55 are moved by the pressing, the distance between the plane movement surface and the inner hollow inner surface of the front link connecting adapter 21 is longer than the diameter of the rotating roller 55, and thus the rotating rollers 55 may be freely rotated. Accordingly, by the rotational movement of the rotating rollers 55, the rear connection link is rotated together with the rotation regulation portion 40, the wire central binding portion 30, the inner connection pipe 61, and the casing pipe 60.

As shown in the drawings, when the pulling force pulling the operating wire 12 forward is removed, the forward/rearward elastic spring 35 compressed toward the front cover 34 moves the forward/rearward movement body, the binding portion fastening pipe 31, the guide piece coupling ring 42, the one side and opposite side guide piece rings 43 and 46, and the one side and opposite side guide pieces 44 and 47 rearward together through elastic restoration force. When each of the one side and opposite side guide pieces 44 and 47 are moved rearward, the protruding rod guide groove 49 is also moved rearward together with the one side and opposite side guide piece 44 and 47. In this case, the pressure protrusion rod 41, which moved the one side and opposite side guide pieces 44 and 47 apart from each other to the left and right groove inner surfaces of the guide piece moving groove 52, respectively, is gradually moved toward the protruding rod guide groove 49 and then seated in the protruding rod guide groove from a fixed and stationary state due to the rearward movement of the one side and opposite side guide pieces 44 and 47. When the pressure protruding rod 41 is seated in the protruding rod guide groove, the one side and opposite side guide pieces 44 and 47 spaced apart from each other come into close contact with each other again. The rotating rollers 55, which have been moved to the center of the horizontal movement surface under the pressing force of the one side and opposite side guide pieces 44 and 47, is moved to the outside of the horizontal movement surface under the elastic restoration force of the elastic pressing piece 54. Since the distance between the horizontal movement surface and the inner surface of the inner hollow of the front link connecting adapter 21 is narrower than the diameter of the rotating rollers 55, the rotating rollers 55 moved to the outside of the horizontal movement surface under the elastic restoration force of the elastic pressing piece 54 is tightly fitted and fixed between the horizontal movement surface, narrower than the diameter of the rotating rollers 55, and the inside of the inner hollow of the front link connecting adapter 21. By fixing the rotating rollers 55, the rotation regulation portion 40, the wire central binding portion 30, the inner connecting pipe 61 and the casing pipe 60 are also fixed in position.

Preferably, as shown in the drawings, a guide surface configured to guide the pressure protruding rod 41 toward the contact surfaces of the one side and opposite side guide pieces 44 and 47 is formed behind the protruding rod guide groove 49 of the one side and opposite side guide pieces 44 and 47. Accordingly, when the operating wire 12 moves forward, the pressure protruding rod 41 may more easily enter and be interposed between the contact surfaces of the one side and opposite side guide pieces 44 and 47.

As described above, the articulated support device 1 according to the present invention may distribute high fixing pressing force among the eight rotating rollers 55 unlike the conventional configuration of fixing through the four rotating rollers 55 in which the high fixing pressing force is concentrated on the four rotating rollers 55, thereby improving the durability of the rotation and fixing units 20. The compression and restoration movement range of the forward/rearward elastic spring 35 is increased by increasing the distance between the front cover 34 and the forward/rearward movement body 32. The length of each guide piece formed behind the protruding rod guide groove 49 is formed to be long, so that a sufficient allowance is provided for the relative movement length of the pressure protruding rod 41 that is relatively moved by exiting from the protruding rod guide groove 49 and being interposed between the one side and opposite side guide pieces 44 and 47, and the movement range of the operating wire 12 may be made longer. Through this, the range of wire pulling that maintains the fixing operation based on the pressing motion of the handle part for releasing the fixing is extended, so that excessive pulling force is not intensively generated in the initial stage of operation. There may be prevented the phenomenon that the operating wire 12 is cut in a short time due to the generation of excessive wire pulling force that is concentrated in the initial stage of the fixed operation. As the forward/rearward movement range of the operating wire 12 for fixing is extended, there may be minimized the inconvenience of assembling the articulated support device 1 in a state in which the operating wire 12 is tightly pulled to maintain the predetermined pulling force of the operating wire 12.

The plurality of links 10 are formed to have an inner hollow. As shown in FIGS. 1 and 8, the front link 10 and the rear link 10 are connected to each other through the rotation and fixing units 20. The handle part 70 is provided on one side of the front of the foremost one of the plurality of links 10, and the fixing portion 13 configured to be detachably coupled to a structure is provided on the other side of the rearmost link. The rear end of the operating wire 12 is fixedly coupled to one side of the rear of the inner hollow of the rearmost one of the plurality of links 10. The front of the operating wire 12 passes through the inner hollow of the plurality of links 10, is wound around the wire fixing ring 36 of each rotation and fixing unit 20, then passes through the wire central binding portion 30, and is connected to the handle part 70.

Furthermore, as shown in FIGS. 1 and 8, the plurality of links 10 may be placed in predetermined directions and then connected by interposing a direction change connection adapter 11 between the link 10 and the rotation and fixing unit 20.

The pressure operation portion 71 is provided on one side of the handle part 70. When the pressure operation portion 71 is pressed, the front of the operating wire 12 is pulled, and the wire and wire central binding portion 30 of each of the rotation and fixing units 20 connecting the plurality of links to each other are moved forward. When the wire central binding portion 30 is moved forward by the forward pulling of the operating wire 12, the rotation regulation portion 40 is released such that it is rotatable in the inner hollow of the forward connection adapter 21. As the rotation regulation portion 40 is released to be rotatable, the wire central binding portion 30, the inner connecting pipe 61, and the casing pipe 60 are released to be rotatable together. As a result, the plurality of links 10 are rotatable relative to each other.

When the pressing force pressing the pressure operation portion 71 of the handle part 70 is removed, the operating wire 12, which has been pulled forward, is moved rearward together with the wire central binding portion 30 by the restoration elastic force of the forward/rearward elastic spring 35 of each of the rotation and fixing units 20. When the wire central binding portion 30 is moved rearward, the rotation regulation portion 40 is fixed not to be rotated in the inner hollow of the forward connection adapter 21. As the rotation regulation portion 40 is fixed, the wire central binding portion 30, the inner connecting pipe 61, and the casing pipe 60 are fixed together. As a result, the plurality of links 10 are fixed not to be rotated relative to each other.

Preferably, as shown in FIGS. 6 and 7, in the handle part 70, a handle body portion 72 is provided with an inner reception space, and is configured such that a pressing operation portion insertion hole 73 is formed therethrough to a predetermined length along the longitudinal direction on one side thereof. A pressure operation portion 71 configured such that the front thereof is inserted and rotatably hinged into the handle body 72 through the pressure operation portion insertion hole 73 and the rear thereof is provided to pass through the pressure operation portion insertion hole 73 and protrude to the outside. An upper pressure roller 74 is rotatably provided on one side of the front of the pressure operation portion 71 inserted into the handle body portion 72. A lower pressure roller 75 is rotatably provided in the handle body portion 72 at a position spaced apart from the upper pressure roller 74 downward by a predetermined distance.

As shown in FIG. 6, in the state in which the front of the operating wire 12 passes between the upper pressing roller 74 and the lower pressing roller 75 while being in contact with the outer surfaces of the rollers and is then fixedly coupled to the inner front of the handle part 70, when the rear of the pressure operation portion 71 protruding to the outside is pressed with a predetermined pressing force and rotated downward around the front hinge coupling portion, the upper pressure roller 74 moves downward together with the pressure operation portion 71, presses the operating wire 12, passing while being in contact with the lower side of the upper pressure roller 74, toward the lower pressure roller 75 and pulls the operating wire 12 forward.

Furthermore, as shown in FIG. 7, when the predetermined pressing force pressing the rear of the pressure operation portion 71 downward is released, the pressure operation portion 71 is moved backward while being relaxed by the elastic restoration force of the wire, and the rears of the upper pressure roller 74 and the pressure operation portion 71 are returned to the upper side.

As described above, the articulated support device 1 according to the present invention enables precise movement and fixing by being linearly moved and immediately fixed to a desired position, and may prevent foreign substances from entering the device during a procedure by sealing the parts where the plurality of links 10 constituting the support device 1 are connected to each other.

In particular, the articulated support device 1 may improve the durability of the rotating and fixing units 20 by distributing the high pressing force, applied onto the rotating rollers 55 provided inside the units 20 for performing rotation and fixing, among the eight rotating rollers 55, and may make the movement range of the operating wire 12 longer, thereby preventing excessive pulling force from being concentrated and generated in the initial stage of the operation in spite of the pressing operation of the handle part for releasing fixing and also preventing the phenomenon that the operating wire 12 is cut in a short time.

Although some embodiments have been described as examples above, the fact that the present invention may be embodied in various forms without departing from the spirit and scope thereof is obvious to those of ordinary skill in the art.

Therefore, the above-described embodiments should be regarded as illustrative rather than restrictive, and all embodiments within the scope of the appended claims and their equivalents are included within the scope of the present invention.

What is claimed is:

1. An articulated support device, the articulated support device being formed to include a plurality of links connected to each other, in which connection portions of the plurality of links are fixed not to move relative to each other or the connection portions of the plurality of links are released to be rotatable relative to each other through an operation of a handle part provided on a front side of the articulated support device, the articulated support device comprising a plurality of rotation and fixing units, wherein each of the plurality of rotation and fixing units comprises:

a front link connection adapter configured such that a front thereof is detachably coupled to an opposite side of a front link;

a wire central binding portion configured such that an operating wire is provided to pass through the wire central binding portion, a forward/rearward movable body provided with a coil spring seating portion therein is provided in the front of the wire central binding portion and is formed to move forward and rearward together with the operating wire, a front cover is provided at a position spaced apart by a predetermined distance in front of the forward/rearward movable body so that it is rotatable in front of the front link connection adapter but does not move forward or rearward, a forward/rearward elastic spring formed of a coil spring is seated on the coil spring seat so that the operating wire passes along a central axis of the elastic spring, and a front surface of the forward/rearward elastic spring is provided to be in contact with a front of an inner side of the front cover and a rear surface of the forward/rearward elastic spring is provided to be in contact with a rear of an inner side of the coil spring seat;

a rotation regulation portion provided on a circumferential surface of the wire central binding portion to be rotated together with the wire central binding portion, and also provided inside the front link connection adapter so that rotational movement is regulated according to forward and rearward the movement of the wire central binding portion;

a casing pipe provided such that a front of a forward connection adapter passes through the casing pipe and protrudes by a predetermined length, also rotatably provided around the forward connection adapter, and configured such that a rear side of the casing pipe is detachably coupled to one side of a rear link; and an inner connection pipe provided such that a front of the wire central binding portion passes through the inner connection pipe and a rear of the wire central binding portion is located inside the inner connection pipe and provided to rotate together with the casing pipe;

wherein the front link and the rear link are connected to each other through the rotation and fixing units, the handle part is provided on one side of a front of a foremost one of the plurality of links and a fixing portion is provided on an opposite side of a rearmost link, a rear end of the operating wire is fixedly coupled to one side of a rear of the rearmost one of the plurality of links, and a front of the operating wire passes through the plurality of links, is wound around a wire fixing ring of each rotation and fixing unit, then passes through the wire central binding portion, and is connected to the handle part;

wherein a pressure operation portion is provided on one side of the handle part so that, when the pressure operation portion is pressed, the front of the operating wire is pulled, and thus a wire and wire central binding portion of each of the rotation and fixing units connecting the plurality of links to each other are moved forward and so that, when the wire central binding portion is moved forward by forward pulling of the operating wire, the rotation regulation portion is released such that it is rotatable in the forward connection adapter, with the result that, as the rotation regulation portion is released to be rotatable, the wire central binding portion, the inner connection pipe, and the casing pipe are released to be rotatable together, so that the plurality of links are rotatable relative to each other; and wherein when pressing force pressing the pressure operation portion of the handle part is removed, the operating wire, which has been pulled forward, is moved rearward together with the wire central binding portion by restoration elastic force of the forward/rearward elastic spring of each of the rotation and fixing units, and, when the wire central binding portion is moved rearward, the rotation regulation portion is fixed not to be rotated in the forward connection adapter, so that, as the rotation regulation portion is fixed, the wire central binding portion, the inner connection pipe, and the casing pipe are fixed together, with the result that the plurality of links are fixed not to be rotated relative to each other.

2. The articulated support device of claim 1, wherein:

a rotating roller seating protrusion is provided to protrude by a predetermined distance in front of the inner connection pipe, a fixing ring coupling protrusion is formed on a front surface of the rotating roller seating protrusion to protrude by a predetermined distance, rotating roller plane movement surfaces are formed on upper, lower, left, and right outer surfaces of the rotating roller seating protrusion, respectively, rotating roller stop protruding surfaces are formed to protrude as predetermined curved surfaces on outer surfaces between the rotating roller plane movement surfaces, and a pressing protrusion rod fixing groove is formed on one side of each of the rotation roller stop protrusion surfaces;

the rotation regulation portion comprises:

a pressure protrusion rod formed as a circular rod having a predetermined length, and configured such that one end thereof is fixedly coupled into the pressure protrusion rod fixing groove;

a guide piece coupling ring fixedly coupled to an outer circumferential surface of the wire central binding portion;

an opposite side guide piece ring formed in a ring shape, rotatably coupled to a rear outer circumferential surface of the guide piece coupling ring, and configured such that four opposite side guide pieces are provided to protrude by a predetermined length rearward at predetermined intervals on a rear of the opposite side guide piece ring and an opposite side protruding rod guide groove is formed in front of the opposite side guide piece;

a one side guide piece ring formed in a ring shape, rotatably coupled to a front outer circumferential surface of the guide piece coupling ring, and configured such that four one side guide pieces are provided to protrude by a predetermined length rearward at predetermined intervals on a rear of the one guide piece ring and are formed to come into contact with one side surface on which the opposite side protruding rod guide groove of the opposite side guide piece is formed and one side protruding rod guide groove is formed in front of a surface in contact with the one side surface on which the opposite side protruding rod guide groove of the opposite side guide piece is formed and is also provided to be opposite to the opposite side protruding rod guide groove;

a fixing ring formed in a ring shape, fixedly coupled to the fixing ring coupling protrusion of the inner connection pipe, is configured such that four rotating roller separation prevention pieces are provided on the outer circumferential surface of the fixing ring at predetermined intervals, guide piece movement grooves are formed between the four rotating roller separation prevention pieces, and a pair of the one side guide piece and the opposite side guide piece vertically pass through the guide piece movement groove and are movable while being spaced apart from each other in the state of being contact with each other until the sides of the respective guide pieces come into contact with left and right groove inner sides of the movement groove;

a rotating roller elastic pressure rib coupled in such a manner that a front thereof comes into contact with and is fixedly coupled to a center of the rear surface of the rotation roller separation prevention piece of the fixing ring, provided along a longitudinal direction of the rotating roller seating protrusion in a center of the horizontal movement surface of the rotating roller, and configured such that a pair of elastic pressing pieces are formed on both left and right sides of the rotating roller elastic pressing rib; and rotating rollers provided on left and right sides of the rotating roller elastic pressing rib along a longitudinal direction, and also provided such that inner sides of the rotating rollers come into contact with the elastic pressing piece and outer sides thereof come into contact with one of the one side guide piece and the opposite side guide piece; and the opposite side protruding rod guide groove and the one side protruding rod guide groove face each other and form a protruding rod guide groove in a state in which the one side and opposite side guide pieces are in contact with each other, and the pressing protruding rod is provided to vertically pass through the protruding rod guide groove and protrude to an outside.

3. The articulated support device of claim 2, wherein:

the handle part comprises:

a handle body portion configured such that a pressing operation portion insertion hole is formed therethrough to a predetermined length along a longitudinal direction on one side thereof;

the pressure operation portion configured such that a front thereof is inserted and rotatably hinged into the handle body through the pressure operation portion insertion hole and a rear thereof is provided to pass through the pressure operation portion insertion hole and protrude to an outside;

an upper pressure roller rotatably provided on one side of a front of the pressure operation portion inserted into the handle body portion; and a lower pressure roller rotatably provided in the handle body portion at a position spaced apart from the upper pressure roller downward by a predetermined distance;

when a front of the operating wire passes between the upper pressing roller and the lower pressing roller while being in contact with outer surfaces of the rollers and is then fixedly coupled to an inner front of the handle part and a rear of the pressure operation portion protruding to an outside is pressed with a predetermined pressing force and rotated downward around a front hinge coupling portion, the upper pressure roller moves downward together with the pressure operation portion, presses the operating wire, passing while being in contact with a lower side of the upper pressure roller, toward the lower pressure roller and pulls the operating wire forward; and when predetermined pressing force pressing a rear of the pressure operation portion downward is released, the pressure operation portion is moved backward while being relaxed by elastic restoration force of the wire, and rears of the upper pressure roller and the pressure operation portion are returned to an upper side.

\* \* \* \* \*